United States Patent
Stangenes et al.

(10) Patent No.: US 9,801,683 B2
(45) Date of Patent: Oct. 31, 2017

(54) UNIVERSAL SHAFT FOR MAGNETIC MANIPULATION OF CATHETERS

(75) Inventors: Todd R. Stangenes, Minneapolis, MN (US); Richard Forrester Duncan, Orange, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 557 days.

(21) Appl. No.: 14/235,615

(22) PCT Filed: Jul. 26, 2012

(86) PCT No.: PCT/US2012/048308
§ 371 (c)(1),
(2), (4) Date: Jul. 7, 2014

(87) PCT Pub. No.: WO2013/019544
PCT Pub. Date: Feb. 7, 2013

(65) Prior Publication Data
US 2014/0316407 A1    Oct. 23, 2014

Related U.S. Application Data

(60) Provisional application No. 61/513,304, filed on Jul. 29, 2011.

(51) Int. Cl.
*A61B 18/18*    (2006.01)
*A61B 18/14*    (2006.01)
(Continued)

(52) U.S. Cl.
CPC ..... *A61B 18/1492* (2013.01); *A61M 25/0127* (2013.01); *A61M 25/0158* (2013.01);
(Continued)

(58) Field of Classification Search
CPC ............ A61B 18/1492; A61B 1/00158; A61B 2018/00029; A61B 2018/00351; A61B 2018/00577; A61B 2018/00791
See application file for complete search history.

(56) References Cited

U.S. PATENT DOCUMENTS

| 6,146,381 A | 11/2000 | Bowe |
| 6,818,299 B2 | 11/2004 | Phillips |

(Continued)

*Primary Examiner* — Michael Peffley
*Assistant Examiner* — Amanda Zink
(74) *Attorney, Agent, or Firm* — Dykema Gossett PLLC (57) ABSTRACT

A magnetically-guided catheter includes a tip positioning magnet in the distal end portion thereof configured to interact with externally applied magnetic fields for magnetically-guided movement. The magnet may be geometrically asymmetric, for example, a C-shape in radial cross-section, so as to allow side-loading of an irrigation fluid lumen and other wire(s) or lines during fabrication. The outer shaft includes a plurality of segments, including a generally soft segment at the distal end thereof for magnetically-guided navigation. The fluid lumen, which extends through the outer shaft, and further extends completely through the magnet for coupling to the ablation electrode irrigation fluid inlet, is constructed so that its mechanical properties (i.e., flexibility) substantially matches that of the outer shaft. The combination of the outer shaft, inner fluid lumen and positioning magnet has interoperability with a broad range of ablation tip assemblies.

16 Claims, 3 Drawing Sheets

(51) Int. Cl.
*A61M 25/01* (2006.01)
*A61B 18/00* (2006.01)
*A61B 1/00* (2006.01)

(52) U.S. Cl.
CPC . *A61B 1/00158* (2013.01); *A61B 2018/00029* (2013.01); *A61B 2018/00351* (2013.01); *A61B 2018/00577* (2013.01); *A61B 2018/00791* (2013.01)

(56) References Cited

U.S. PATENT DOCUMENTS

| | | | |
|---|---|---|---|
| 7,341,063 B2 * | 3/2008 | Garbibaldi | A61B 1/00158 128/899 |
| 7,892,233 B2 * | 2/2011 | Hall | A61B 5/0422 600/374 |
| 2002/0156430 A1 | 10/2002 | Haarala | |
| 2004/0097803 A1 | 5/2004 | Panescu | |
| 2007/0016131 A1 * | 1/2007 | Munger | A61M 25/0127 604/95.05 |
| 2009/0306655 A1 | 12/2009 | Stangenes | |
| 2010/0168559 A1 | 7/2010 | Tegg | |
| 2010/0174177 A1 | 7/2010 | Wu | |
| 2011/0118582 A1 | 5/2011 | de la Rama | |
| 2012/0035605 A1 * | 2/2012 | Tegg | A61B 18/1492 606/41 |

* cited by examiner

UNIVERSAL SHAFT FOR MAGNETIC MANIPULATION OF CATHETERS

CROSS-REFERENCE TO RELATED APPLICATIONS

This application claims the benefit of U.S. provisional application No. 61/513,304, filed 29 Jul. 2011, which is hereby incorporated by reference as though fully set forth herein.

BACKGROUND OF THE INVENTION a. Field of the Invention

The present disclosure relates generally to medical instruments, and more specifically, to catheters navigable within the body of a patient using externally applied magnetic fields.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature to the intended site, for example, a site within the patient's heart, and carries one or more electrodes, which may be used for mapping, ablation, diagnosis, or other treatments. Precise positioning of the catheters within the body of the patient is desirable for successful completion of the above procedures. In general, such catheters may be complex in their construction and therefore difficult (and expensive) to manufacture.

To position a catheter within the body at a desired site, some type of navigation must be used, such as using mechanical steering features incorporated into the catheter (or an introducer sheath). Another approach has been developed, namely, providing magnetically guided catheter devices that are navigated through the patient's body using externally-generated magnetic fields. More specifically, magnetic stereotactic systems have been developed that are particularly advantageous for positioning of catheters, as well as other devices, into areas of the body. The externally-generated magnetic fields and gradients are generated to precisely control the position of the catheter within the patient's body. Such stereotactic systems operate by monitoring the position of the catheter tip in response to the applied magnetic fields and, using well established feedback and control algorithms, controlling the fields so that the catheter tip is guided to and positioned in a desired location within the patient's body. Once positioned, physicians may operate the catheter, for example, to ablate tissue to interrupt potentially pathogenic heart rhythms or to clear a passage in the body.

However, the magnetic response of the catheter in such magnetic guidance systems can be a limitation on the precise control of a catheter. Improvements in catheters utilized with magnetic guidance and control systems, such as stereotactic systems, are desired. Specifically, a low cost, yet high performance magnetically guided catheter is desirable.

As further background, it is known generally that catheter ablation (e.g., RF ablation) may generate significant heat, which if not controlled can result in undesired or excessive tissue damage, such as steam pop, tissue charring, and the like. It is therefore common (and desirable) to include a mechanism to irrigate the target area and the device with biocompatible fluids, such as a saline solution. The use of irrigated ablation catheters can also prevent the formation of soft thrombus and/or blood coagulation. There are two general classes of irrigated electrode catheters, i.e., open irrigation catheters and closed irrigation catheters. Closed ablation catheters usually circulate a cooling fluid within the inner cavity of the electrode. Open ablation catheters typically deliver the cooling fluid through open outlets or openings on or about an outer surface of the electrode. Open ablation catheters often use the inner cavity of the electrode, or distal member, as a manifold to distribute saline solution, or other irrigation fluids, to one or more passageways that lead to openings/outlets provided on the surface of the electrode. The saline thus flows directly through the outlets of the passageways onto or about the distal electrode member.

One challenge in developing a magnetically-guided, open-irrigated ablation catheter, however, is how to deploy a tip positioning magnet so as to avoid contact with the irrigation fluid. This challenge stems from the fact that the magnetic material that would typically be used in the tip positioning magnet is highly susceptible to corrosion when exposed to irrigation fluid. It would therefore be desirable to provide a magnetically-guided catheter design that prevents material corrosion by creating a distinct separation between the irrigation fluid and the magnetic material.

In addition, it would be desirable to have a catheter shaft and tip positioning magnet configurations that have broad applicability to a number of irrigated ablation tip electrode configurations already in existence, thereby reducing cost and other resources in adapting the shaft, irrigation lumen and other features (e.g., ablation electrode and thermocouple wiring) to achieve interoperability.

The foregoing discussion is intended only to illustrate the present field and should not be taken as a disavowal of claim scope.

BRIEF SUMMARY OF THE INVENTION

One advantage of the methods and apparatus described, depicted and claimed herein, in embodiments suitable for use in magnetically-guided irrigated ablation catheters, involves an improved tip positioning magnet configuration that allows easy integration with irrigated ablation catheter features, such as with a fluid lumen, power and temperature sensing wires, and the like. Another advantage involves a shaft configuration, in embodiments suitable for use in magnetically-guided irrigated ablation catheters, that allow interoperability with a broad range of irrigated ablation tip assemblies, thereby reducing or eliminating the cost and complexity of adapting existing tip assemblies.

A distal apparatus for an irrigated ablation catheter includes a tip positioning magnet and a tip electrode assembly. The magnet extends along an axis, has proximal and distal ends and a passage extending through the magnet between the proximal and distal ends. The passage is configured to receive a fluid lumen. The tip assembly is distally disposed relative to said magnet and includes an ablation surface. The tip assembly further includes an inlet configured to receive the lumen. The tip assembly also includes a passageway coupled to the inlet and including an outlet disposed at an external surface of the tip assembly for delivery of the fluid. In an embodiment, the magnet is geometrically asymmetric, and in a further embodiment, the magnet is C-shaped.

A shaft arrangement for an irrigated ablation catheter includes an outer shaft, a tip positioning magnet, and a fluid lumen. The shaft comprises flexible tubing and has a proximal end and a distal end. The distal end is configured to be coupled to a tip irrigation ablation electrode assembly. The magnet is disposed inside the shaft at the distal end. The magnet has an axis and is configured to respond to an externally-applied magnetic field. The magnet also includes a passage that extends axially therethrough. The fluid lumen extends through the shaft from the proximal end and extends completely through the passage of the magnet, where the extreme distal end of the fluid lumen is configured for connection to an inlet of the tip assembly. The shaft includes a plurality of shaft segments, each having a respective flexibility associated therewith. The lumen also includes a plurality of segments with a respective flexibility associated therewith. The shaft segments and lumen segments are disposed, axially, relative to each other so as to match the overall flexibility of the lumen with that of the shaft and/or minimize its contribution to the overall shaft stiffness. The shaft arrangement can be used with a broad range of irrigated tip ablation electrode assemblies.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 6 is a cross-sectional view of a proximal portion of the fluid lumen of FIG. 2, showing inner and outer jacket portions with braided material in between.

DETAILED DESCRIPTION OF THE INVENTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figures 1, 2:
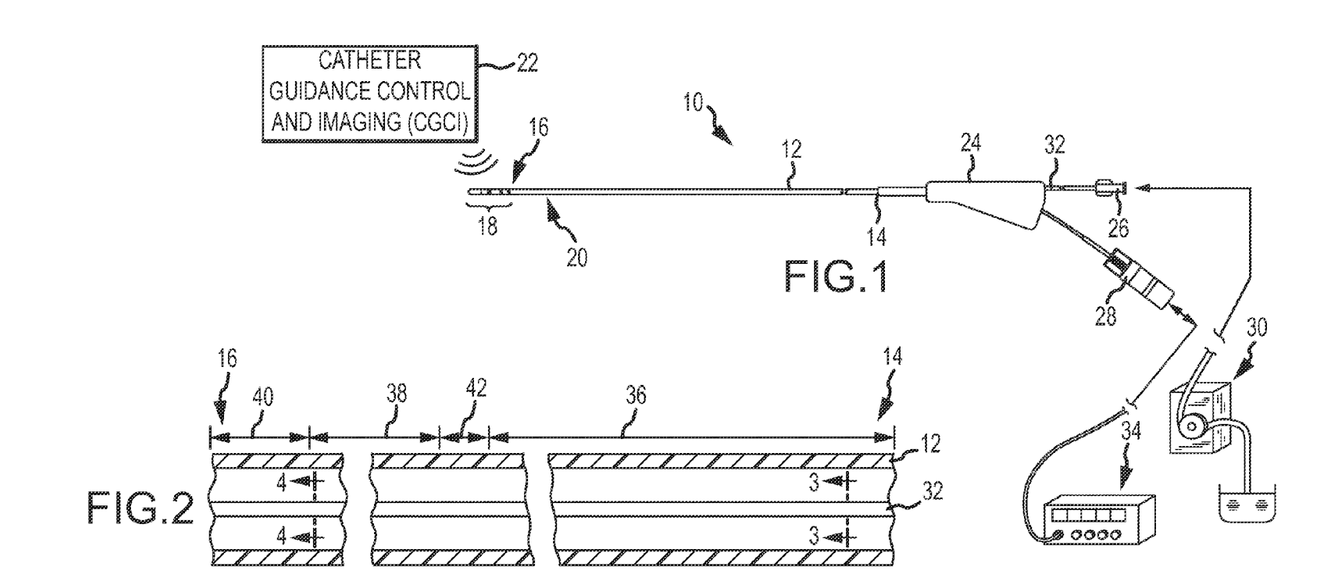
FIG. 1 is a plan view of an exemplary magnetically-guided catheter.
FIG. 2 is an enlarged, partial cross-sectional view of a shaft and a fluid lumen portion of the catheter of FIG. 1.

Referring now to the drawings wherein like reference numerals are used to identify identical or similar components in the various views, FIG. 1 is a simplified, isometric view of a magnetically guided electrode catheter 10 operatively adapted for conducting a diagnostic or a therapeutic procedure under clinician control. In the illustrated embodiment, catheter 10 is an irrigated ablation catheter. Catheter 10 generally includes a flexible shaft 12 in the form of a flexible outer tube or tubing (shaft). The shaft 12 has a proximal end portion 14 and a distal end portion 16. The catheter 10 further includes a distal tip electrode assembly 18 disposed at distal end 16. The shaft 12 further includes a plurality of segments of differing construction and flexibility, including at least a relatively flexible distal segment 20. The segment 20 is configured so as to facilitate navigation of the catheter 10 through the use of externally-applied magnetic fields (i.e., by a catheter guidance control and imaging block 22) interacting with a tip positioning magnet (best shown in FIG. 7) in the catheter tip, as described in greater detail below. Of course, the segment 20 can be fabricated with a variety of different degrees of flexibility.

Catheter 10 further includes a Y connector 24, a luer device 26, and an electrical connector 28. Luer device 26 is used to provide an interface for a flow path so that fluid can be selectively passed through the Y-connector 24 for delivery by tip assembly 18 (i.e., for irrigation purposes). Alternatively, device 26 can be a stopcock (not shown) for opening and closing the flow path. FIG. 1 shows, for example, an irrigation fluid pump 30 (coupled to a source of irrigation fluid) coupled to the luer device 26, which in turn may be coupled to a fluid lumen 32. In one configuration, the fluid lumen 32 is contained within the outer shaft 12, and extends from the proximal end 14 to the distal end 16, where it is received at the tip assembly 18.

Electrical connector 28 is configured to establish electrical connection(s) between a power source (e.g., RF ablation power) and/or other external electrical/electronic apparatus, as shown diagrammatically as an electronic apparatus 34, to facilitate, for example, ablation procedures, mapping or pacing procedures, or to perform other aspects of a medical procedure.

Y-connector 24 separates the inner, fluid lumen 32 from electrical lead wires which together extend from the tip assembly 18 and entering the Y-connector 24. More specifically, lumen 32 and the lead wires located forward of Y-connector 24 pass internally through outer shaft 12, while aft of Y-connector 24, the lumen (inner tube) 32 and the lead wires are separated for connection to the fluid source 30 and the power source/electronics 34, respectively. Electrical connector 28 may comprise a known connector configured to engage the external electronics 34 with, for example, a plug-in connection. One suitable electrical connector is a 14 pin REDEL® plastic connector commercially available from LEMO of Rohnert Park, Calif., although other connectors from various manufacturers may likewise be utilized.

The fluid source 30 and the RF ablation generator (e.g., represented by block 34) are generally well known to those of skill in the art. For example, the fluid source 30 can comprise various known assemblies, including fixed volume rolling pumps, variable volume syringe pumps and other pump assemblies known to those skilled in the art, including a gravity fed supply. The fluid provided by fluid source 30 may comprise a suitable biocompatible fluid, such as saline. The RF ablation generator may comprise conventional apparatus, such as a commercially available unit sold under the model number IBI-1500T RF Cardiac Ablation Generator, available from Irvine Biomedical, Inc. Of course, the RF ablation generator can also comprise other known energy sources. It should be understood that ablation catheter systems may, and typically will, include other structures and functions omitted herein for clarity, such as one or more body surface electrodes (skin patches) (e.g., an RF dispersive indifferent electrode/patch for RF ablation). In the case of a mapping catheter (or mapping function incorporated into an ablation catheter), the electronics apparatus 34 can include visualization, mapping and navigation components known in the art, including among others, for example, an EnSite™ Velocity™ system running a version of NavX™ software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., hereby incorporated by reference in its entirety as though fully set forth herein. Additionally, an electrophysiological (EP) monitor or display such as an electrogram signal display or other systems conventional in the art may also be coupled (directly or indirectly).

Before proceeding to the detailed description, a brief overview of a contemplated use of the disclosed embodiments will first be set forth. The tip assembly 18 contained in the catheter 10 is of the type that includes at least one positioning magnet. The tip positioning magnet is configured to cooperate with externally-generated magnetic fields to provide for the guidance (i.e., movement) of the catheter tip to a desired location within the body. Thus, in operation, catheter 10, specifically the distal tip thereof, may be navigated to a site in the body to perform a medical procedure, such as an atrial mapping, pacing and/or ablation. For example only, the catheter distal tip may extend into a heart chamber of a patient. Once the distal tip is disposed within the heart chamber, a magnetic field is applied by CGCI 22, which interacts with the tip positioning magnet, particularly the magnetic field produced by the tip magnet, to exert an orienting force on the tip assembly, allowing for precise positioning of the catheter distal tip. The externally-generated magnetic fields used to orient the distal tip may be, in one embodiment, generated using a magnetic stereotactic system (e.g., as shown in block form as CGCI 22 in FIG. 1). Such stereotactic systems are known in the art and are commercially available from, for example only, Stereotaxis, Inc. of St. Louis, Mo. and Maple Grove, Minn. Such systems may include movable source magnets outside the body of the patient and operative details of such systems are disclosed in, for example, U.S. Pat. Nos. 6,475,223 and 6,755,816, the disclosures of which are hereby incorporated by reference in their entirety. In addition, U.S. application Ser. No. 11/953,615, filed 10 Dec. 2007, (PG PUB 2008/0091193 A1 published on Apr. 17, 2008) also discloses a guidance system, and is also hereby incorporated by reference as though fully set forth herein. While catheter 10 may be advantageously used with a stereotactic system, the invention contemplates that magnetic fields and gradients to deflect the catheter distal tip may be alternatively generated by other systems and techniques.

FIG. 2 is a partial cross-sectional view of shaft 12 and fluid lumen 32 contained therein. Details concerning the tip assembly 18 and other structures associated with the catheter 10 have been omitted for clarity. Flexible shaft 12 may be fabricated according to known processes, such as multilayer processing including extrusion processes, mandrel-based processes and combinations thereof from any suitable, biocompatible tubing material known in the art of medical instruments, such as engineered nylon resins and plastics, including but not limited an elastomer commercially available under the trade designation PEBAX® from Arkema, Inc. of a suitable durometer, melting temperature and/or other characteristics.

In one embodiment, the shaft 12 includes at least three distinct segments. The most proximal segment of the shaft 12, designated segment 36, comprises material having a relatively high hardness (e.g., ~70 D (Durometer)) and thus increased stiffness, and includes braided material for kink reduction. The next segment 38 is relatively more flexible than segment 36 and is non-braided. Segment 38 may comprise material having a reduced hardness (e.g., ~35 D). The next segment 40 is slightly more rigid than segment 38, and is also non-braided (e.g., ~40 D). The segment 40 is the distal most segment and is configured to be coupled to the tip assembly 18.

In an embodiment, an additional segment 42 may be provided as a transition segment and is in between segments 36 and 38 (i.e., between the 70 D and 35 D segments). Segment 42 can have an intermediate flexibility as well, for example, an intermediate hardness (e.g., ~50 D) The transition segment 42 provides relatively high bond strength between the braided and non-braided segments 36, 38. It should be understood that segments having different durometer levels can be used to adjust the flexibility of the shaft in order to restrict or expand the range of motion. Overall, the relatively soft distal segments of shaft 12 allow for precise positioning of the tip without having to overcome relative stiffness that exists in the proximal portion of the shaft 12.

First segment 36 extends for a majority of the axial length of shaft 12 between proximal end portion 14 and distal end portion 16. Second segment 38 extends for a shorter length than the length of first segment 36, and third segment 40 extends for a length that can be shorter than the length of second segment 38. While there are a wide variety of configurations, adapted to any specific application, the shaft 12 may be about 52.525 inches (128 cm) in length with the soft segments 38, 38 being about 5.375 inches (13.7 cm) in length. It should be understood, however, that the relative, axial lengths of each segment, as shown in FIG. 2, are for illustration purposes only and not intended to be suggestive or limiting in nature.

In a still further embodiment, the different segments of shaft 12 can share a common outer diameter, such as 7 F (French) in size, with the distal end 16 configured for a press-fit connection or the like to the tip assembly 18. Of course, variations in this regard are also possible.

Fluid lumen 32 is configured to extend through the length of the outer shaft 12 and is configured to deliver irrigation fluid or other fluid sourced at the proximal end (e.g., from source 30) to the distal end 16, to the tip assembly 18. The mechanical properties (e.g., flexibility) of lumen 32 vary axially along its length so as to substantially match the mechanical properties (e.g., flexibility) of the shaft 12 and/or minimize its contribution to the overall shaft stiffness. The proximal portion of the lumen 32 (i.e., corresponding to the proximal shaft segment 36) is stiffer than the distal portion of the lumen 32 (i.e., corresponding to the relatively flexible distal shaft segments 38, 40 and optionally 42), which is relatively more flexible. In an embodiment, the variation in the mechanical properties (i.e., flexibility) is achieved by varying the wall thickness of the tubing used for lumen 32. In a further embodiment, either one of the shaft or the lumen can have differing flexibilities along its axial length (e.g., the lumen can be very flexible along its length, with the shaft having a plurality of segments each having a respect hardness, as described herein).

Figure 3:
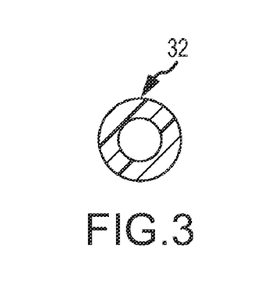
FIGS. 3-4 are cross-sectional views, taken substantially along lines 3-3 and 4-4 in FIG. 2, showing different wall thicknesses and thus different flexibility levels for the fluid lumen.
Figure 4:
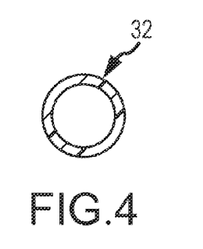

FIGS. 3 and 4 are cross-sectional views of lumen 32 taken substantially along lines 3-3 (proximal portion) and 4-4 (distal portion) in FIG. 2, respectively. As shown in FIG. 3, lumen 32 has an increased wall thickness, for increased stiffness, as compared to the cross-section of lumen 32 in FIG. 4, which has a decreased wall thickness for decreased stiffness (increased flexibility).

Figure 5:
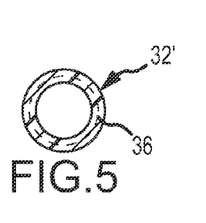
FIG. 5 is a cross-sectional view of a proximal portion of the fluid lumen of FIG. 2, showing a braided portion thereof.

FIG. 5 is a cross-sectional view of lumen 32 in a further embodiment, designated 32', which includes braided material 36. The braided material 36 is included in the proximal portion of lumen 32'. In a still further embodiment, the braiding material 36 (if present) may be varied as well (i.e., by varying the pick count) to make the proximal portion stiffer and the distal section relatively more flexible. In addition, the braided material also provides increase wall strength, minimizing the potential for the tubing to kink or collapse. All of the foregoing approaches may be used either alone or in combination. Conventional materials may be used for lumen 32. In an embodiment, lumen 32 comprises polyimide material. In particular, another feature of the lumen 32 is that only the proximal portion of the lumen 32 has polyimide and the distal portion of the lumen 32 does not have polyimide in it so that the distal portion is relatively more flexible.

Figure 6:
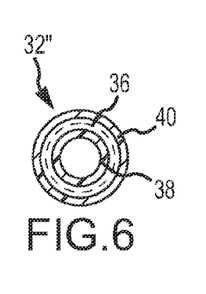

FIG. 6 is a cross-sectional view of a still further embodiment of lumen 32, designated lumen 32", which uses jackets (i.e., inner jacket 38 and outer jacket 40) on either side of the braiding material 40 to control the flexibility of the lumen and to ensure it is water-tight. Such jackets may comprise conventional materials, for example only, an elastomer commercially available under the trade designation PEBAX®, an aliphatic polyether polyurethane commercially available under the trade designation TECOFLEX® or other similar material.

In an alternative embodiment, the lumen 32 may comprise a relatively soft PEBAX® extrusion without braiding to provide additional flexibility but less column strength, or may comprise a plurality of PEBAX® extrusions (i.e., with a stiffer proximal portion), which would then be bonded together (not shown).

Figures 7, 8, 9A, 9B, 9C, 9D:
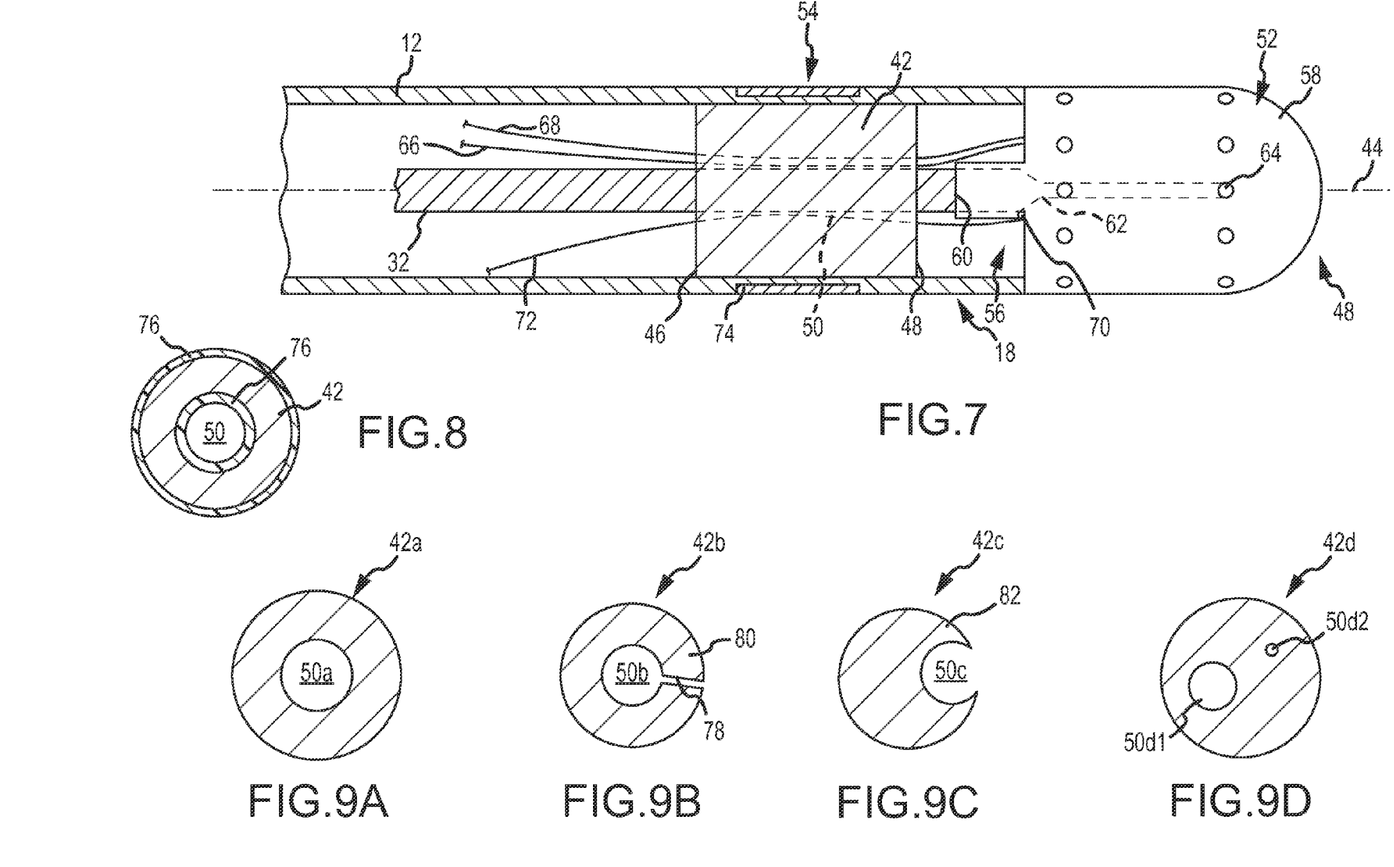
FIG. 7 is a cross-sectional view of an exemplary distal tip electrode assembly suitable for use in the catheter of FIG. 1.
FIG. 8 is a cross-sectional view of the tip positioning magnet of FIG. 7, having a protective coating on both the inner and outer surface of the magnet.
FIGS. 9A-9D are cross-sectional views of several embodiments of the tip positioning magnet of FIG. 7.

FIG. 7 is an enlarged, cross-sectional side view showing tip electrode assembly 18 and a tip positioning magnet 42. The positioning magnet 42 is generally cylindrical in shape and is configured to respond to an externally-applied magnetic field, such as that applied by CGCI block 22 (best shown in FIG. 1). The magnet 42 is disposed along an axis 44 and has proximal and distal ends 46, 48, respectively. The magnet 42 further includes a passage 50 extending between proximal and distal ends 46, 48. The passage 50 is configured to at least receive fluid lumen 32, and, as illustrated, (1) to allow the lumen 32 to extend completely through the passage 50 to emerge distal of the distal end 48, and (2) to allow, in an embodiment, the electrode conductor wire(s), temperature sensor wire(s) and a safety line (all as described below) to also pass completely through.

The tip assembly 18 includes a tip electrode 52 and a ring electrode assembly 54. The tip electrode 52 includes a proximal portion 56 and a selectively active ablation surface 58. The proximal portion 56 is configured for coupling to the wall of shaft 12, particularly to distal most shaft segment 40. The ablation surface 58, however, remains exposed even as incorporated into catheter 10, and thus is configured to present an electrically conductive surface, for example, for electrical interaction with tissue (i.e., ablation, mapping, etc.). In one embodiment, ablation electrode 52 comprises, for example, a 7 F (i.e., diameter), 4 mm (i e, length) exposed tip portion, although variations are possible as one of ordinary skill in the art will appreciate.

The ablation electrode 52 can generally comprise electrically and potentially thermally, conductive materials, as known to those of ordinary skill in the art. Examples of suitable electrically conductive materials include (but are not limited to) gold, platinum, iridium, palladium, stainless steel, and various mixtures, alloys and combinations thereof. In one embodiment, the ablation surface 58 can be rounded (e.g., partially spherical or hemispherical), although other configurations may be used.

The tip assembly 18 is forward (distal) of positioning magnet 42 and, in the illustrated embodiment, the ablation electrode 52 thereof includes an inlet 60 configured to receive fluid lumen 32. The electrode 52 further includes at least one irrigation passageway, such as passageway 62 shown in dashed line form in FIG. 7, coupled to the inlet 60 and having an outlet, such as outlet 64, disposed on at an external surface (i.e., ablation surface 58) of the electrode 52. The electrode 52 can thus comprise any one of a plurality of irrigated ablation tip electrodes known in the art. It should be understood features have been omitted from FIG. 7 for clarity. For example, while FIG. 7 shows a single passageway 62 to a single outlet port 64, this is a simplification—the passageway ends just inside the proximal end of the tip electrode wherein the plurality of outlet ports shown are all in fluid communication with the passageway so as to allow fluid to flow into the tip and out of all of the outlet port at once. In this way, the tip electrode can act like a fluid manifold.

In another embodiment, the tip assembly 18 can also include an annular ring component (i.e., a manifold) disposed proximal of the ablation electrode 52 and distal of the tip positioning magnet 42. Such a manifold (not shown in FIG. 7) can provide additional proximal irrigation capabilities, such as providing proximal irrigation between the magnet 42 and the ablation electrode 52.

Ablation electrode 52 is electrically connected to a conductor 66 (e.g., a wire), which wire 66 extends through the shaft 12 to the proximal end 14 for termination at connector 28. Apparatus 34 (e.g., RF ablation generator), when coupled to wire 66, is configured to selectively energize the ablation electrode 52 in accordance with any known ablation strategy. Wire 66 can comprise conventional materials and construction (e.g., 34 AWG wire, insulated, solderable).

FIG. 7 further shows a safety line 68. The line 68 is configured to restrain and/or limit stretching of the soft segment 20 of shaft 12 that may otherwise occur through repeated advance/retract cycles of catheter 10. The line 68 also provides additional assurance that tip assembly 18 will not disconnect from the catheter 10 (i.e., from the shaft 12). In an exemplary embodiment, a high tensile strength LCP (liquid crystal polymer) fiber wire may be used as line 68, or alternatively, line 68 may comprise a high strength fibrous material, for example, a para-aramid synthetic fiber commercially available under the trademark KEVLAR® from E.I. du Pont de Nemours and Company, Wilmington, Del., U.S.A., as seen by reference to U.S. application Ser. No. 12/850,485, filed 4 Aug. 2010, which is hereby incorporated by reference as though fully set forth herein. One end of line 68 may be affixed or anchored at Y-connector 24 or alternatively wound around the shaft at the proximal hub. The line 68 is also affixed at the distal end portion specifically to tip electrode 52.

The tip assembly 18 can further include a temperature sensor 70, which can take the form of a thermocouple or thermistor, as known in the art. Sensor 70 is electrically connected to one or more conductor(s) 72, which extend through the shaft 12 to the proximal end 14, for termination at electrical connector 28. Like the power conductor 66, the temperature sensor wire(s) 72 can then be connected to an ablation power generator (shown as block 34 in FIG. 1) for use as feedback during an ablation procedure, or coupled to another electronic apparatus for processing the temperature indicative signal from the sensor 70 to compute a temperature.

The ring electrode assembly 54 can include one or more ring electrodes 74 (shown in dashed line form in FIG. 7). Like the ablation electrode 52, the ring electrode(s) 74 remain exposed even as incorporated into catheter 10 and thus present an electrically conductive surface, for example, for mapping, localization and the like. When one or more ring electrode(s) 74 are present, a corresponding number of electrical conductors (not shown) are included to connect the ring electrode 74 to the electrical connector 28 (and thereafter to electrical/electronic apparatus 34). Generally, ring electrode(s) 74 can comprise conventional materials and can be provided in any number, widths, and/or inter-electrode spacing. Such ring electrode(s) 74 can be swaged onto the outside diameter (OD) surface of the shaft 12, and can be positioned directly radially-outwardly of the positioning magnet 42, or alternatively, axially offset from the location of the positioning magnet 42. This swaging configuration also helps secure the magnet/lumen/tip assembly into place within the shaft by potentially pinching the shaft over the location of the magnet.

With continued reference to FIG. 7, positioning magnet 42 can be a permanent magnet fabricated from a known magnetic materials, such as ferromagnetic materials, or in alternative embodiments, fabricated from compositions including rare-earth materials, such as neodymium-iron boron—43 (NdFeB-43), neodymium-iron boron—45 (NdFeB-45), neodymium-iron boron—48 (NdFeB-48), neodymium-iron boron—50 (NdFeB-50), or, preferably, neodymium-iron-boron—55. Magnet 42, in an NdFeB-55 embodiment, can be between about 0.400 and 0.600 inches in axial length. It should be understood that a plurality of such magnets (not shown), each axially reduced in length compared to magnet 42, can be used instead, for example, with spacers and/or springs disposed in between adjacent magnets.

It should be understood, however, that the construction of magnet 42 can vary in grade, material, and size (i.e., length, diameter, wall thickness, etc). For example, other magnet material compositions can be used; however, it should be appreciated that any particular selection of an alternate magnetic material composition will involve a balancing of the resultant magnetic field strength of the tip positioning magnet versus the externally-generated magnet field strength developed by the external magnetic guidance systems (i.e., the resulting force developed on the catheter tip for guidance is a function of both magnetic field strength levels).

FIG. 8 is a cross-sectional view of magnet 42. The magnet 42 includes a coating 76 that comprise a relatively high dielectric constant material, such as a material commercially available under the trade designation PARYLENE (i.e., poly(p-xylylene) polymers) or other similar material. The coating 76 is configured to isolate the magnetic material from any outside moisture and/or electrical current. The coating 76 inhibits corrosion that can otherwise occur due to contact with irrigation fluid or body fluid(s). In an embodiment, the coating 76 is on all inner and outer surfaces of the magnet 42.

Referring again to FIG. 7, the positioning magnet 42, as shown, is disposed inside of shaft 12. The passage 50 is configured in size and shape so as to allow the fluid lumen 32, the power wire 66, the safety line 68, the thermocouple wire(s) 72 and any other wire(s) or materials to pass therethrough.

FIGS. 9A-9D are cross-sectional views of embodiments of tip positioning magnet 42, with coating 76 omitted for clarity. The embodiments of magnet 42 exhibit various cross-sectional configurations that allow (in different ways) the fluid lumen 32, and the various wires/lines to extend completely therethrough. In addition, these configurations tend to maximize the amount of magnetic material (i.e., mass), while allowing passage of the fluid lumen and/or other wire(s)/line(s).

FIG. 9A shows a first embodiment of the tip positioning magnet, designated magnet 42a. Magnet 42a represents a first configuration that includes a single, centrally-disposed passage 50a configured in size and shape so as to allow fluid lumen 32, and wires/lines 66, 68 and 72 to extend completely therethrough. In the NdFeB-55 embodiment described above, passage 50a has a diameter of approximately 0.045", sufficient to perform the function noted above.

FIG. 9B shows a second embodiment of the tip positioning magnet, designated magnet 42b. Magnet 42b represents a second configuration that also includes a centrally-disposed passage 50b configured in size and shape so as to allow fluid lumen 32 to extend completely therethrough, but in addition includes an axially-extending slot 78 between the passage 50b and an external surface 80 of magnet 42b. The slot 78 is configured to provide additional space for various wire(s)/lines described above to connect to components or structures on either axial side of magnet 42b, and to assist in the manufacturing process. Such wire(s)/lines could either float in slot 78 or be bonded in place.

FIG. 9C shows a third embodiment of the tip positioning magnet, designated magnet 42c. Magnet 42c represents a third configuration that includes a passage 50c whose axis is offset relative to main axis 44, where the passage 50c radially opens up to an external surface 82 of magnet 42c, to thereby form a substantially C-shaped tip positioning magnet (when taken in radial cross-section). The passage 50c is configured in size and shape so as to allow fluid lumen 32 and wire(s)/lines 66, 68 and 72 to axially extend completely therethrough. Advantageously, the lumen 32 and wire(s)/line can be inserted from the side, radially into passage 50c.

FIG. 9D shows a fourth embodiment of the tip positioning magnet, designated magnet 42d. Magnet 42d represents a fourth configuration that includes two separate passages 50d1 and 50d2. Passage 50d1 is configured in size and shape so as to allow fluid lumen 32 to extend completely therethrough, while passage 50d2 is configured in size and shape to allow wire(s)/lines 66, 68 and 72 to extend completely therethrough.

The embodiments of tip positioning magnet 42 allow for different amounts of mass to be deployed in the magnet, and allow for different sizes and numbers of lumens, wire(s), line(s) or other materials to axially extend through the magnet. In addition, the embodiments of FIGS. 9B-9D exhibit asymmetric geometry, which can result in a non-linear movement or unexpected curvature of the catheter in response to an externally-applied magnetic field. In such embodiments, the guidance control (e.g., CGCI 22) must be appropriately configured to adjust the applied external magnetic field to compensate.

The positioning magnet 42, in an embodiment, is polarized along axis 44 (proximal-distal axis), having a north (N) pole (i.e., from which magnetic field lines extend) at the distal end portion and a south (S) pole (i.e., to which magnetic field lines terminate) at the proximal end portion. Alternatively, the positioning magnet 42 can be polarized along an axis different than axis 44 (see FIG. 11A), or as required by any particular navigation system. The distal end 48 of positioning magnet 42 can be placed relatively close to the distal end of shaft 12 (i.e., 0.100"). It should be understood, however, that this distance is exemplary only and not limiting in nature.

The foregoing combination of shaft, fluid lumen and tip positioning magnet can be used as a universal building block for the efficient manufacture of a magnetically guided catheter. Many tip electrode assemblies can be directly used or easily adapted with such a building block, for subsequent use in a magnetically guided navigation system.

It should be further understood that with respect to the irrigated ablation catheter 10, variations are possible with respect to the number, size and placement of the irrigation passageways and corresponding irrigation ports. For example, the disclosure contemplates catheters configured to provide a plurality of cavities and/or passageways adapted to facilitate the flow of irrigation fluid therethrough to the manifold's outer surface (proximal irrigation) as well as to the distal ablative surface for delivery by the distal irrigation passageways (distal irrigation). The disclosure further contemplates lateral or side discharge irrigation passageways and ports, angled (e.g., at an acute angle with respect to the main longitudinal axis of the electrode assembly) passageways and ports as well as distal irrigation passageways and ports. The disclosure still further contemplates various further arrangements, for example, where the irrigation passageways are substantially equally distributed around the circumference of the manifold to provide substantially equal distribution of fluid. It should be understood that the art is replete with various configurations and design approaches for proximal and distal irrigation passageways and ports, and will therefore not be further elaborated upon.

Figure 10A:
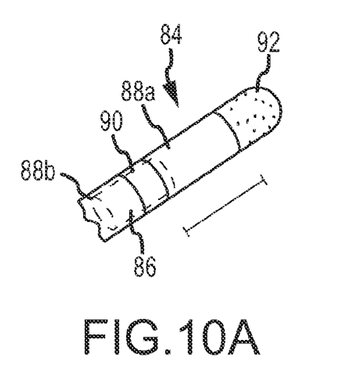
FIGS. 10A-10B are isometric views of a flexible distal portion of a magnetically-guided catheter having a single positioning magnet, in un-deflected and deflected conditions, respectively.
Figure 10B:
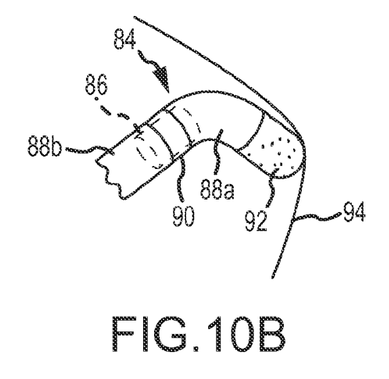

FIGS. 10A-10B are isometric views of a distal portion of a magnetically guided ablation catheter 84, in non-contact and contact conditions, respectively. Referring to FIG. 10A, catheter 84 incorporates a distal catheter shaft design that includes segments of varying flexibility to achieve specific mechanical properties or curve shapes. The catheter 84 includes a single positioning magnet 86 contained in shaft 88 (i.e., which in turn has at least first and second shaft segments 88a, 88b), a ring electrode 90 and a distal tip ablation electrode 92. Shaft segment 88a has a first flexibility that is greater than a second flexibility of shaft segment 88b. By decreasing the stiffness of the shaft segment between the ring electrode 90 and the tip electrode 92, the behavior (shape) of the catheter 84 will change when it comes into contact with tissue. A number of points warrant emphasizing.

First, the tip of the catheter 84 will buckle when too much force is exerted on the tissue by the catheter 84, thereby avoiding a potentially unsafe condition.

Second, by placing a ring electrode 90 at the location of the positioning magnet 86, the distance between the ring electrode 90 and the tip electrode 92 can be measured and used to monitor the behavior of the catheter 84. The distance between these two points will decrease (e.g., as measured with an electro-anatomical mapping system, such as EnSite™ Velocity™ described above), which decrease in distance can indicate that the catheter 84 (i.e., tip thereof) has come into contact with the tissue. This contact is shown in FIG. 10B, where the catheter 84 is contacting tissue 94, and has buckled. This information (i.e., detection of a contact condition, the decrease in distance, curve, etc.) could additionally be used to provide feedback to a navigation system that is guiding the catheter 84 to the tissue surface.

Third, when the catheter tip starts to buckle, the tip electrode 92 will move from a position perpendicular to the tissue to one that is parallel. This may be desired to more safely or effectively deliver energy to the tissue through the tip during ablation. It may also help in the creation of a "drag lesion" in which the catheter tip is moved along the tissue surface in a consistent, sweeping motion. When used with a remote navigation system, this catheter configuration may be ideal to ensure consistent, predictable lesion creation.

Fourth, this configuration may also provide an approach to maintaining tissue contact in a beating heart. The method comprises the steps of advancing the catheter to contact the target tissue, advancing the catheter further until the distal section buckles, and then maintaining that location either mechanically with a guiding introducer or a remote navigation system. In this scenario, the proximal end of the catheter would be stable relative to the tissue and as the heart beats, so the distal section of the catheter would flex and bend in response to the movement of the heart wall.

Figure 11A:
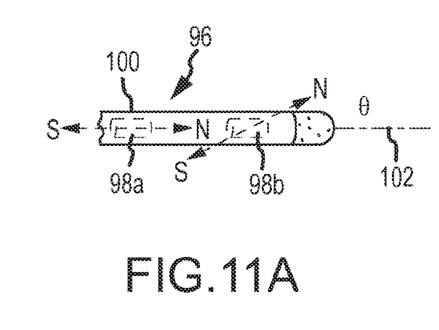
FIGS. 11A-11B are isometric views of a flexible distal portion of a magnetically-guided catheter having two positioning magnets, in un-deflected and deflected conditions, respectively.
Figure 11B:
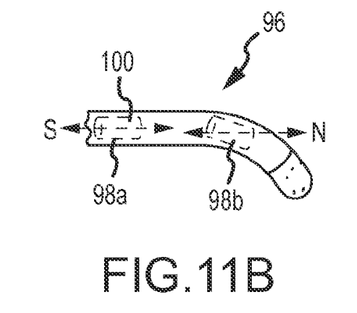

FIGS. 11A-11B are isometric views of a dual magnet catheter 96, in un-deflected and deflected conditions. Catheter 96 includes first and second positioning magnets 98a, 98b embedded within the shaft 100. Each magnet 98a, 98b includes a respective axis of polarity, as shown in FIG. 11A. The polarity of the most proximal magnet 98a is axial relative to the catheter shaft 100 while the axis of polarity of the distal magnet 98b is slightly off-axis (i.e., at an angle of θ). When both magnets 98a, 98b subjected to a consistent magnetic field, the result will be a curved catheter shaft, as shown in FIG. 11B. In the absence of a magnetic field, or while constrained within a sheath (not shown), the catheter shaft will behave based on the mechanical properties of the shaft alone. This concept can be extended to include multiple magnets to achieve varying curve shape, including spiral catheters, or can be reversed—a pre-formed, curved catheter than becomes straight when subjected to a magnetic field.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A distal apparatus for an irrigated ablation catheter, comprising:
a positioning magnet having an axis, proximal and distal ends and a passage therebetween configured to receive a fluid lumen, said positioning magnet being geometrically asymmetric relative to the axis; and
a tip electrode assembly distally disposed relative to said magnet and including an ablation surface, said tip electrode assembly including an inlet configured to receive the fluid lumen, said tip electrode assembly further including a passageway coupled to the inlet for receiving fluid and having at least one outlet disposed at an external surface of said tip electrode assembly for delivering fluid;
wherein said positioning magnet is selected from the group comprising (i) a first configuration wherein the passage of said positioning magnet is centrally-disposed and includes an axially-extending slot between the passage and an external surface of said positioning magnet; (ii) a second configuration wherein the passage of said positioning magnet is offset relative to the axis and opens to the external surface thereby forming a substantially C-shaped magnet; and (iii) a third configuration wherein the passage of said positioning magnet is a first passage that is offset relative to the axis and configured to allow the fluid lumen to extend completely therethrough, said positioning magnet further including a second passage that is offset from the axis configured to allow a wire to extend therethrough and wherein said second passage does not extend to said external surface of said positioning magnet.

2. The apparatus of claim 1 wherein said positioning magnet comprises one of a permanent magnet and a permanent magnet comprising rare earth elements.

3. The apparatus of claim 2 wherein said positioning magnet comprises neodymium iron boron (NdFeB) material.

4. The apparatus of claim 1 further comprising a dielectric coating substantially surrounding all surfaces of said positioning magnet.

5. The apparatus of claim 1 wherein said tip electrode assembly includes a manifold disposed distal of said positioning magnet and an ablation electrode distal of said manifold, said ablation electrode having the ablation surface, the fluid lumen being coupled to said manifold.

6. The apparatus of claim 5 further including a temperature sensor in sensing proximity to said ablation electrode, a first electrical conductor connected to said ablation electrode for energizing said electrode, at least a second electrical conductor electrically connected to said temperature sensor, the passage of said positioning magnet being further configured to allow said first and second electrical conductors to extend completely therethrough.

7. The apparatus of claim 1 further comprising at least one ring electrode.

8. A shaft arrangement for an irrigated ablation catheter, comprising:
a shaft comprising flexible tubing having a proximal end and a distal end wherein the distal end is configured for coupling to a tip electrode assembly;
a magnet disposed inside said shaft at the distal end, said magnet having an axis and configured to respond to an externally-applied magnetic field, said magnet including a passage extending axially therethrough; and
fluid lumen tubing comprising a fluid lumen extending through said shaft from the proximal end and completely through the passage of said magnet and configured for connection to an inlet of said tip electrode assembly;
said shaft including a plurality of shaft segments each having a respective hardness associated therewith, said fluid lumen tubing having a plurality of lumen segments each having a respective hardness associated therewith, the shaft segments and the lumen segments being axially disposed relative to each other so as to match the flexibility of said fluid lumen tubing with that of said shaft.

9. The shaft arrangement of claim 8 wherein said fluid lumen tubing has a wall thickness, the lumen segments comprising different wall thickness values.

10. The shaft arrangement of claim 8 wherein a proximal one of the lumen segments includes braided material to thereby decrease flexibility.

11. The shaft arrangement of claim 8 wherein a proximal one of the lumen segments of said fluid lumen tubing comprise inner and outer jackets of an elastomeric material between which braided material is disposed.

12. The shaft arrangement of claim 8 wherein the shaft segments comprise respective materials having different durometer levels.

13. The shaft arrangement of claim 8 wherein a distally penultimate shaft segment is the most flexible shaft segment.

14. The shaft arrangement of claim 8 wherein proximal segments of said fluid lumen tubing comprise polyimide material, which polyimide material is absent from one or more of distal segments of said fluid lumen tubing.

15. A catheter, comprising:
- a shaft having a distal-most shaft segment having a first flexibility and a proximal segment;
- a first tip positioning magnet in said shaft in said distal-most shaft segment, said first tip positioning magnet having a first polarizing axis associated therewith;
- a second tip positioning magnet in said shaft in said distal-most shaft segment, said second tip positioning magnet having a second polarizing axis associated therewith that is different than said first polarizing axis of said first tip positioning magnet;
- wherein said second tip positioning magnet is movable relative to said first tip positioning magnet such that when said catheter is subjected to a consistent magnetic field, said first and second tip positioning magnets move relative to each other so that said second polarizing axis and said first polarizing axis align wherein said distal-most shaft segment deflect.

16. The catheter of claim 15 wherein said distal-most shaft segment is pre-curved in the absence of a magnetic field, wherein when said catheter is subjected to said consistent magnetic field, said pre-curved distal-most shaft segment is straightened.

* * * * *